United States Patent [19]

Zielinski

[11] Patent Number: 5,075,426
[45] Date of Patent: Dec. 24, 1991

[54] PENTADIENYLLUTETIUM COMPLEX

[75] Inventor: Matthew B. Zielinski, Yorba Linda, Calif.

[73] Assignee: Union Oil Company of California, Los Angeles, Calif.

[21] Appl. No.: 546,527

[22] Filed: Jun. 29, 1990

Related U.S. Application Data

[63] Continuation-in-part of Ser. No. 380,143, Jul. 14, 1989, abandoned.

[51] Int. Cl.$^5$ ............................................. C07F 5/00
[52] U.S. Cl. ....................................................... 534/15
[58] Field of Search ........................................... 534/15

[56] References Cited

U.S. PATENT DOCUMENTS 3,152,157 10/1964 Shapiro et al. ............... 534/15 X
4,668,773 5/1987 Marks et al. ..................... 534/15

Primary Examiner—Robert L. Stoll
Assistant Examiner—Cynthia Harris
Attorney, Agent, or Firm—Gregory F. Wirzbicki; Michael A. Kondzella

[57] ABSTRACT

A pentadienyllutetium complex is prepared by reacting a source of 2,4-dimethylpentadienyl anions with a source of trivalent lutetium cations.

26 Claims, 1 Drawing Sheet

PENTADIENYLLUTETIUM COMPLEX

This application is a continuation-in-part of Ser. No. 380,143, filed July 14, 1989, abandoned, which is incorporated herein by reference.

FIELD OF THE INVENTION

This invention relates to coordination complexes of lanthanide metals. In one of its more particular aspects, it relates to a pentadienyllutetium complex.

BACKGROUND OF THE INVENTION

Hydrocarbyl complexes of the lanthanide metals complexes, such as LiLn(allyl)$_4$·dioxane (Ln=lanthanide), have been shown to catalyze the polymerization of 1,3-butadiene.

SUMMARY OF THE INVENTION

The present invention provides a novel complex of lutetium. This complex has the formula ($\eta^5$—(CH$_3$)$_2$C$_5$H$_5$)Lu($\eta^5$—,$\eta^3$—(CH$_3$) C$_5$H$_5$CH$_2$CH$_2$CH(CH$_3$)C$_3$H$_3$(CH$_3$)). It is prepared by reaction of 2,4-dimethylpentadienylpotassium and lutetium trichloride. The complex may be useful as a diene polymerization catalyst.

DESCRIPTION OF THE PREFERRED EMBODIMENTS

Figure 1:
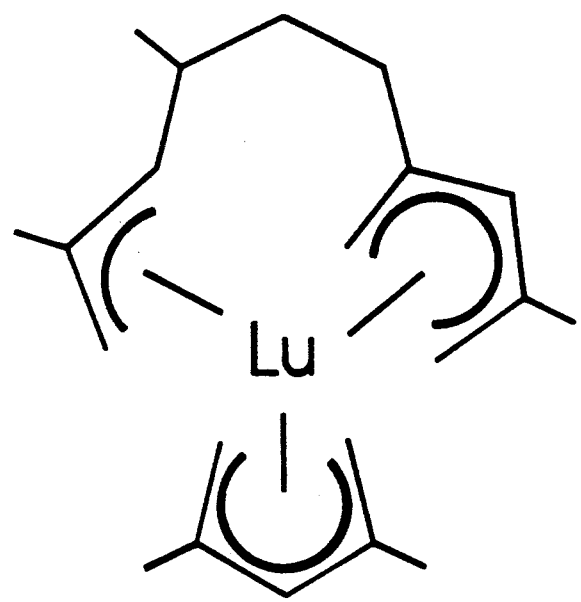
FIG. 1 is a structural formula of the pentadienyllutetium complex of the present invention.

The pentadienyllutetium complex of the present invention has the formula ($\eta^5$—(CH$_3$)$_2$C$_5$H$_5$)Lu($\eta^5$—,$\eta^3$—(CH$_3$) C$_5$H$_5$CH$_2$CH$_2$CH(CH$_3$)C$_3$H$_3$(CH$_3$)). Its structural formula is shown in FIG. 1. From the structural formula it can be seen that a lutetium atom is $\eta^5$-complexed with one solitary 2,4-dimethylpentadienyl ligand; the lutetium atom is also complexed with one 2,4-dimethylpentadienyl dimer via $\eta^3$-allyl and $\eta^5$-pentadienyl bonding.

Figure 2:
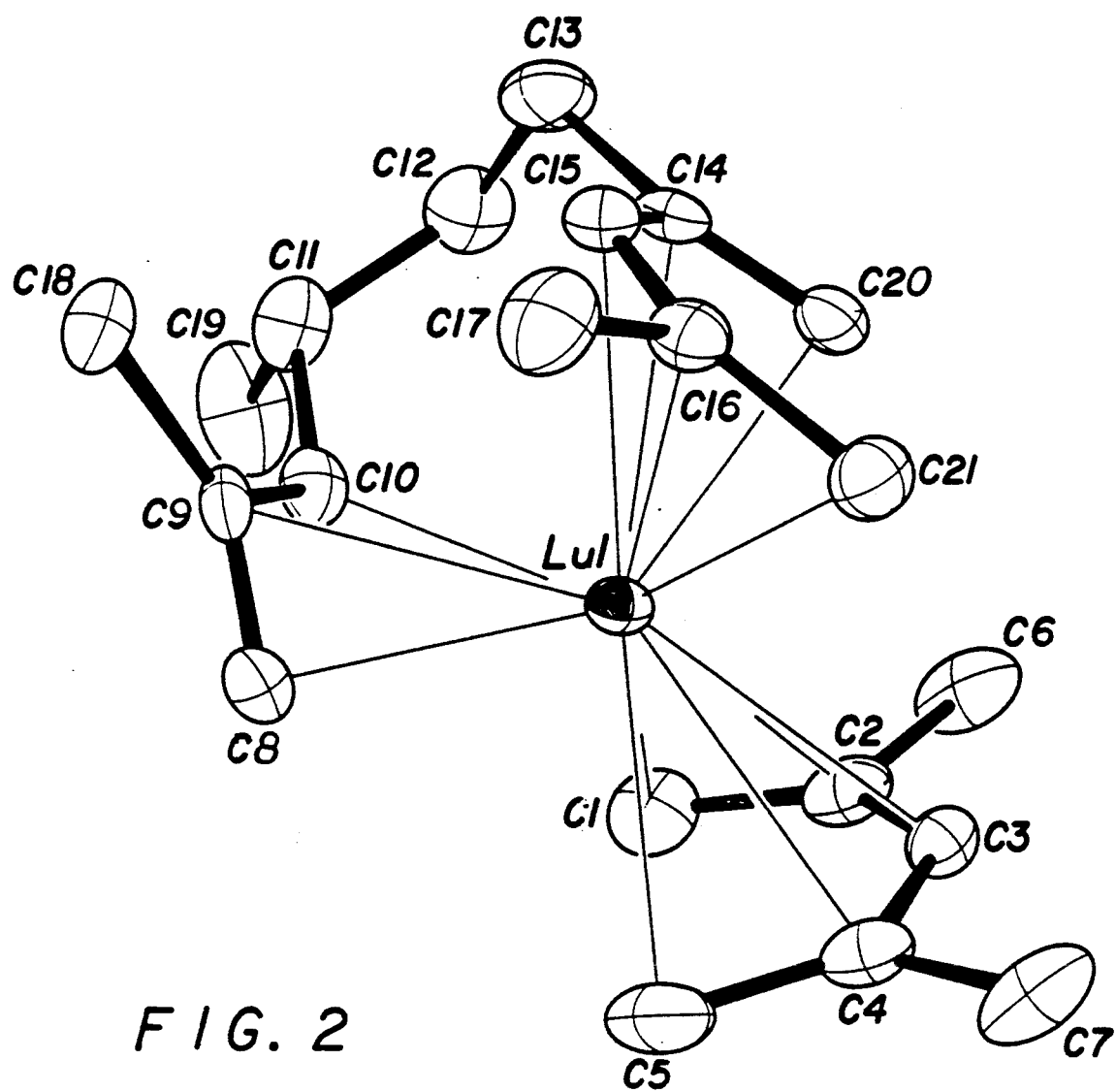
FIG. 2 is an ORTEP (Oak Ridge Thermal Ellipsoid Plot) diagram of the pentadienyllutetium complex of the present invention.

The structure of the pentadienyllutetium complex of the present invention is further illustrated in the ORTEP diagram shown in FIG. 2, wherein each of the carbon atoms is numbered. An ORTEP diagram, derived from X-ray crystallographic data, shows the spatial relationships of the atoms within a molecule and indicates the probability of location of the atoms at a specific point in space by means of ellipsoids. The ORTEP plot is shown at the 30 percent probability level.

An unusual feature of the novel pentadienyllutetium complex of the present invention is that the lutetium atom is complexed by one 2,4-dimethylpentadienyl ligand as well as by one 2,4-dimethylpentadienyl dimer.

The pentadienyllutetium complex of the present invention is prepared by means of a metathesis reaction which involves the addition of three equivalents of 2,4-dimethylpentadienylpotassium to one equivalent of lutetium trichloride. Any organic solvent which is nonreactive with the reactants and in which the reactants are sufficiently soluble can be used, but an ether solvent such as tetrahydrofuran (THF) is preferred. The reaction is preferably carried out at low temperatures; for example, at temperatures in the range of about $-40°$ C. to about $-100°$ C.; a temperature of about $-78°$ C. is especially preferred. Because of the acute air sensitivity and moisture sensitivity of the organometallic product of this reaction, it is desirable to conduct the metathesis reaction under an inert gas such as argon. Reaction times of about 1 hour to about 2 hours are effective. Work-up of the reaction product can be accomplished by allowing the reaction mixture to warm to room temperature, vacuum evaporating the solvent, extracting the residue with an inert solvent such as hexane, cyclohexane, or heptane, and concentrating the resulting extract. The concentrated extract yields a crystalline product upon cooling. The crystalline product has been found to have the formula ($\eta^5$—(CH$_3$)$_2$C$_5$H$_5$)Lu($\eta^5$—,$\eta^3$—(CH$_3$) C$_5$H$_5$CH$_2$CH$_2$CH(CH$_3$)C$_3$H$_3$(CH$_3$)), the structural formula shown in FIG. 1 and the ORTEP diagram shown in FIG. 2.

The present invention will be better understood by reference to the following examples which are included for purposes of illustration and are not to be construed as in any way limiting the scope of the present invention, which is defined in the appended claims.

EXAMPLE 1

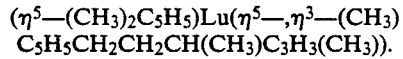

($\eta^5$—(CH$_3$)$_2$C$_5$H$_5$)Lu($\eta^5$—,$\eta^3$—(CH$_3$) C$_5$H$_5$CH$_2$CH$_2$CH(CH$_3$)C$_3$H$_3$(CH$_3$)).

Into a 100-mL, three-necked, round-bottom flask equipped with a spinbar, rubber septum, glass stopper and gas inlet was placed 1.50 g (5.33 mmol) of anhydrous lutetium trichloride and 20 mL of THF. Argon was introduced through the gas inlet. The assembly was attached to a Schlenk line and the solution was stirred overnight to disperse the undissolved salt. Into a 50-mL, single-necked, round-bottom flask was placed a solution containing 2.15 g (16.0 mmol) of 2,4-dimethylpentadienyl-potassium prepared according to the method of Yasuda, H.; Ohnuma, Y.; Yamauchi, M.; Tani, H.; Nakamura, A., *Bull. Chem. Soc. Jpn.* 1979, 52, 2036, in 30 mL of THF. The flask was stoppered with a rubber septum and removed to the Schlenk line. This light amber-colored solution was slowly syringed into the rapidly stirred slurry of lutetium trichloride, previously cooled to $-78°$ C. Upon dropwise addition of the potassium salt solution, a localized yellow color appeared momentarily, then dissipated. This occurred until approximately 1 mL of solution had been added. The yellow color then remained as the balance of the potassium salt was added. After complete addition, the solution was stirred for an additional 1.5 hr. The cooling bath was then removed and the solution was allowed to warm slowly to room temperature. During this period the solution gradually turned dark brown. After stirring overnight, the solvent was vacuum evaporated. The residue was extracted with hexane (4×20 mL) and the resulting extract was concentrated to a volume of 30 mL. The solution was then cooled to $-78°$ C. for 8 hr, which resulted in the formation of olive-colored crystals. These crystals were isolated and subsequently dissolved in a minimum amount of THF/hexane. The solution was cooled to ca. $-30°$ C. overnight, resulting in the formation of pale orange-yellow crystals suitable for X-ray diffraction analysis; yield 0.13g (5.3%). IR (Nujol mull) absorptions were observed at 3110 (vw), 3090 (w), 3080 (w), 3025 (w), 1525 (s, br), 1425 (sh), 1350 (w), 1340 (w), 1320 (vw), 1290 (w), 1270 (w), 1250 (w-m), 1230 (w), 1210 (vw), 1180 (w), 1155 (vw), 1090

(w-m), 1060 (m), 1030 (m), 1015 (w), 990 (sh), 980 (w), 945 (w), 925 (w), 890 (w), 875 (w, br), 850 (w-m), 835 (w-m), 810 (s), 800 (w), 795 (w), 770 (s, br), 700 (sh), 690 (sh), 630 (m), 600 (w) and 565 (sh) cm$^{-1}$. Anal. Calcd for LuC$_{21}$H$_{33}$: Lu, 38.00%. Found: Lu, 37.8%.

EXAMPLE 2

NMR Spectra of ($\eta^5$—(CH$_3$)$_2$C$_5$H$_5$)Lu($\eta^5$—,$\eta$-3—(CH$_3$)C$_5$H$_5$CH$_2$CH$_2$CH(CH$_3$)C$_3$H$_3$(CH$_3$)).

$^1$H and $^{13}$C NMR spectra were acquired at ambient temperature with an IBM AF-270 FT NMR narrow-bore spectrometer. All data processing was done on an Aspect-3000 computer using DISNMR standard software. A 5 mm dual tuned probe was used to observe $^1$H and $^{13}$C nuclei at 270.130 and 67.925 MHz, respectively. The 90° pulse widths for $^1$H and $^{13}$C were 8.6 and 4.6 μsecs, respectively, while the decoupler coil pulse length was measured to be 14.2 μsecs. The lutetium complex was dissolved in benzene-d$_6$ solvent in a 5 mm Wilmad glass NMR tube and the sample was sealed under vacuum. The chemical shifts are reported in ppm from TMS by setting the residual proton signal of the solvent at 7.15 ppm and the corresponding $^{13}$C solvent resonance at 128.0 ppm. The chemical shifts are shown in Table I.

TABLE I $^{13}$C{$^1$H} and $^1$H NMR solution spectra in benzene-d$_6$ for (C$_7$H$_{11}$)Lu(C$_{14}$H$_{22}$).

| Carbon | | Chemical Shifts | |
|---|---|---|---|
| No. [a, b] | Type | $^{13}$C | $^1$H (multiplicity, proton count) |
| 1 | CH$_2$ | 81.1 | 3.68(s, 1H) |
|   |        |      | 2.68(s, 1H) |
| 2 | C | 147.3 | — |
| 3 | CH | 90.0 | 4.73(s, 1H) |
| 4 | C | 145.2 | — |
| 5 | CH$_2$ | 82.2 | 4.35(s, 1H) |
|   |        |      | 3.37(s, 1H) |
| 6 | CH$_3$ | 30.0 | 1.86(s, 3H) |
| 7 | CH$_3$ | 29.9 | 1.98(s, 3H) |
| 8 | CH$_2$ | 59.5 | 1.95(m, 1H) |
|   |        |      | 1.51(d, 1H, J=4.59Hz) |
| 9 | C | 151.3 | — |
| 10 | CH | 80.9 | 3.58(d, 1H, J=7.64Hz) |
| 11 | CH | 33.8 | 2.46(m, 1H) |
| 12 | CH$_2$ | 44.3 | 1.75(m, 1H) |
|    |        |      | 1.25(m, 1H) |
| 13 | CH$_2$ | 41.5 | 2.73(m, 1H) |
|    |        |      | 1.93(m, 1H) |
| 14 | C | 155.0 | — |
| 15 | CH | 98.0 | 4.63(s, 1H) |
| 16 | C | 149.0 | — |
| 17 | CH$_3$ | 27.7 | 1.82(s, 3H) |
| 18 | CH$_3$ | 24.2 | 2.23(s, 3H) |
| 19 | CH$_3$ | 24.0 | 1.07(d, 3H, J=6.63Hz) |
| 20 | CH$_2$ | 73.0 | 3.12(s, 1H) |
|    |        |      | 3.01(s, 1H) |
| 21 | CH$_2$ | 76.0 | 2.95(s, 1H) |
|    |        |      | 2.61(s, 1H) |

[a] refers to carbon numbering scheme shown in FIG. 2
[b] signal assignments for atoms 1 through 7 were made based on inference from a combination of 2D NMR experiments and X-ray data Carbon signal multiplicities were determined using the J-modulated spin echo pulse sequence. A 2D $^1$H COSY spectrum was acquired using Jeener's two pulse sequence 90°-t1-45°-ACQ(t2), minimizing the diagonal peak intensities, according to Nagayama, K.; Kumar, A.; Wuthrich, K.; Ernst, R. R., J. Mac. Res. 1980, 40, 321. Thirty two scans were collected over a spectral width of 2,703 Hz for each of 256 time increments to give a matrix of 1024×1024 data points. The recycle delay used was 2 secs. The long range COSY experiment used the pulse sequence of Bax, A.; Freeman, R., J. Mag. Res. 1981, 44, 542, 90°-t1-Δ-45°-Δ-ACQ(t2), under the same conditions but with Δ set to 80 msecs to observe weak cross peaks from long range couplings. The free induction decays were multiplied with an unshifted sine squared bell function and symmetrization was applied to the final spectrum.

A 2D heteronuclear correlation spectrum (XHCORR) according to Bax, A.; Morris, G.; J. Mac. Res. 1981, 42, 501, was recorded using the pulse sequence, 90° (H)-½ t1-180° (C)-½t1-D3-90° (C)90° (H)d4-ACQ(t2/) (under proton decoupling). The acquisition involved 128 scans for each of 128 t1 increments using a 3 sec recycle delay. Delays D3 and D4 were optimized for J=160 Hz (i.e. set to 3.125 and 1.563 msec, respectively). The spectral widths used in the F1 and F2 domains were 2,702 and 13,514 Hz, respectively. The t2 data were exponentially weighed using a line-broadening factor of 5 Hz and Fourier transformed over 2,048 data points. The t1 interferograms were modified with a shifted ($\pi$/4) sine bell squared function before Fourier transformation over 256W data points as a magnitude spectrum. Finally, the pulse sequence that worked best for obtaining a long range heteronuclear correlation spectrum of this organometallic complex was the modified version of XHCORR suggested in Krishnamurthy, V. V.; Nunlist, R., J. Mac. Res. 1988, 80, 280. The sequence involves the elimination of the refocusing D4 delay and BB decoupling during acquisition. The D3 delay was optimized for long range couplings of the magnitude of 8 Hz and set to be 62.5 msec. The number of scans was increased to 512 for each increment of t1.

EXAMPLE 3

X-ray Crystallography of ($\eta^5$—(CH$_3$)$_2$C$_5$H$_5$)Lu($\eta^5$—,$\eta$-3—(CH$_3$)C$_5$H$_5$CH$_2$CH$_2$CH(CH$_3$)C$_3$H$_3$(CH$_3$)).

A single crystal of approximate dimensions 0.20×0.30×0.40 mm was sealed into a thin-walled glass capillary under an inert atmosphere (N$_2$) and mounted on a Syntex P2$_1$ diffractometer. Subsequent setup operations (determination of accurate unit cell dimensions and orientation matrix) and collection of room temperature (296 K) intensity data were carried out using standard techniques similar to those of Churchill, M. R.; Lashewycz, R. A.; Rotella, F. J., Inorg. Chem. 1977, 16, 265. Details appear in Table II.

TABLE II

Crystal Data and Structure Refinement Parameters for (C$_7$H$_{11}$)Lu(C$_{14}$H$_{22}$).

Formula: C$_{21}$H$_{33}$Lu
Fw: 460.5
Crystal System: Triclinic
Space Group: P1
a = 7.382(4) Å
b = 8.703(2) Å
c = 16.443(6) Å
α = 78.54(2)°
β = 84.74(4)°
γ = 68.11(3)°
V = 960.5(6) Å$^3$
Z = 2
D$_{calcd}$, Mg/m$^3$ = 1.592
Diffractometer: Syntex P2$_1$
Radiation: MoKα (λ = 0.710730 Å)
Monochromator: Highly oriented graphite

TABLE II-continued

Crystal Data and Structure Refinement Parameters for $(C_7H_{11})Lu(C_{14}H_{22})$.

Data Collected: +h, ±GK,±l
Scan Type: θ-2θ
Scan Width: 1.2 deg.
Scan Speed: 2.0 deg min$^{-1}$ (in ω)
$2\theta_{max}$, deg: 55.0
μ(Mo Kα), mm$^{-1}$ = 5.144
Absorption correction: Semi-Empirical (ψ-scan method)
Reflections Collected: 4439
Reflections with $|F_o| > 0$: 4380
No. of Variables: 200
$R_F = 3.3\%$; $R_{wF} = 4.8\%$
Goodness of Fit: 1.23

All 4439 data were corrected for the effects of absorption and for Lorentz and polarization effects and placed on an approximately absolute scale by means of a Wilson plot. Any reflection with I(net)<0 was assigned the value $|F_o|=0$. A careful examination of a preliminary data set revealed no systematic extinctions nor any diffraction symmetry other than the Friedel condition. The centrosymmetric triclinic space group P$\bar{1}$[C$^1_i$; No. 2] was chosen and later determined to be correct by successful solution of the structure.

All crystallographic calculations were carried out using either our locally modified version of the UCLA Crystallographic Computing Package (UCLA Crystallographic Computing Package, University of California Los Angeles, 1981, C. Strouse; personal communication) or the SHELXTL PLUS program set (Nicolet Instrument Corporation; Madison, WI 1988). The analytical scattering factors for neutral atoms were used throughout the analysis (International Tables for X-Ray Crystallography; Kynoch Press: Birmingham, England, 1974; pp 99-101); both the real (Δf') and imaginary (iΔf'') components of anomalous dispersion (International Tables for X-Ray Crystallography; Kynoch Press: Birmingham, England, 1974; pp 149-150) were included. The quantity minimized during least-squares analysis was $\Sigma w(|F_o|-|F_c|)^2$ where $w^{-1}=\sigma^2(|F_o|)+0.0007(|F_o|)^2$.

The structure was solved by direct methods (MITHRIL) (Gilmore, C. J., J. Appl. Cryst. 1984, 17, 4246.) and refined by full-matrix least-squares techniques (SHELXTL). Hydrogen atom contributions were included using a riding model with d(C-H)=0.96Å and U(iso)=0.08Å$^2$. Refinement of positional and anisotropic thermal parameters led to convergence with $R_F=3.3\%$; $R_{wF}=4.8\%$ and GOF=1.23 for 200 variables refined against all 4380 unique data, ($R_F=3.1$; $R_{wF}=4.6$ for those 4185 data with $|F_o|>6.0$ σ($|F_o|$)). A final difference-Fourier map was devoid of significant features, ρ (max)=1.37eÅ$^{-3}$.

Atomic coordinates and equivalent isotropic displacement coefficients are listed in Table III. Selected interatomic distances and angles are listed in Table IV. Anisotropic displacement coefficients are shown in Table V while H-atom coordinates and isotropic displacement coefficients are shown in Table VI.

TABLE III

Atomic coordinates (×10$^4$) and equivalent isotropic displacement coefficients (Å$^2$ × 10$^4$) for $(C_7H_{11})Lu(C_{14}H_{22})$

| | x | y | z | U(eq)* |
|---|---|---|---|---|
| Lu(1) | −2242.5(.2) | 347.4(.2) | 2205.9(.1) | 273.5(.9) |
| C(1) | 361(9) | −1464(7) | 3336(3) | 549(21) |
| C(2) | −164(7) | −2687(6) | 3091(3) | 469(17) |
| C(3) | −167(7) | −2961(6) | 2291(3) | 406(15) |
| C(4) | 481(7) | −2203(6) | 1517(3) | 448(16) |
| C(5) | 1181(8) | −921(8) | 1419(4) | 603(22) |
| C(6) | −974(10) | −3737(7) | 3761(4) | 741(24) |
| C(7) | 256(10) | −2858(8) | 771(4) | 657(24) |
| C(8) | −1403(7) | 2854(6) | 1785(3) | 454(17) |
| C(9) | −2849(7) | 3468(5) | 2387(3) | 376(15) |
| C(10) | −2798(7) | 2535(6) | 3187(3) | 434(17) |
| C(11) | −4231(10) | 3020(8) | 3887(3) | 558(23) |
| C(12) | −5561(10) | 1993(9) | 4090(3) | 607(25) |
| C(13) | −6885(8) | 2158(8) | 3381(3) | 553(21) |
| C(14) | −5909(6) | 1106(6) | 2721(3) | 402(16) |
| C(15) | −5981(6) | 2044(5) | 1896(3) | 374(14) |
| C(16) | −5152(6) | 1483(6) | 1143(3) | 385(15) |
| C(17) | −5375(9) | 2847(7) | 391(3) | 557(21) |
| C(18) | −4531(9) | 5100(6) | 2112(3) | 509(19) |
| C(19) | −3045(14) | 2756(12) | 4668(4) | 951(47) |
| C(20) | −4972(7) | −585(6) | 2951(3) | 444(17) |
| C(21) | −4058(7) | −142(6) | 1046(3) | 450(17) |

*Equivalent isotropic U defined as one third of the trace of the orthogonalized U$_{ij}$ tensor

TABLE IV

Selected Interatomic Distances (Å) and Angles (Deg) for $(C_7H_{11})Lu(C_{14}H_{22})$.

| Interatomic Distances | | | |
|---|---|---|---|
| Lu(1)-C(1) | 2.620(6) | Lu(1)-C(2) | 2.703(4) |
| Lu(1)-C(3) | 2.693(4) | Lu(1)-C(4) | 2.740(5) |
| Lu(1)-C(5) | 2.677(6) | Lu(1)-C(8) | 2.440(6) |
| Lu(1)-C(9) | 2.656(5) | Lu(1)-C(10) | 2.629(5) |
| Lu(1)-C(14) | 2.636(5) | Lu(1)-C(15) | 2.642(4) |
| Lu(1)-C(16) | 2.658(5) | Lu(1)-C(20) | 2.567(5) |
| Lu(1)-C(21) | 2.614(6) | Lu(1)-Cent(1) | 2.227 |
| Lu(1)-Cent(2) | 2.353 | Lu(1)-Cent(3) | 2.149 |
| C(1)-C(2) | 1.398(10) | C(2)-C(3) | 1.383(8) |
| C(2)-C(6) | 1.514(9) | C(3)-C(4) | 1.439(7) |
| C(4)-C(5) | 1.371(10) | C(4)-C(7) | 1.497(9) |
| C(8)-C(9) | 1.412(6) | C(9)-C(10) | 1.398(6) |
| C(9)-C(18) | 1.515(6) | C(10)-C(11) | 1.504(7) |
| C(11)-C(12) | 1.533(12) | C(11)-C(19) | 1.551(11) |
| C(12)-C(13) | 1.541(9) | C(13)-C(14) | 1.515(8) |
| C(14)-C(15) | 1.432(6) | C(14)-C(20) | 1.362(7) |
| C(15)-C(16) | 1.423(7) | C(16)-C(17) | 1.508(7) |
| C(16)-C(21) | 1.376(6) | | |
| Interatomic Angles | | | |
| C(1)-C(2)-C(3) | 127.1(5) | C(1)-C(2)-C(6) | 116.7(5) |
| C(3)-C(2)-C(6) | 116.0(6) | C(2)-C(3)-C(4) | 130.8(5) |
| C(3)-C(4)-C(5) | 125.4(5) | C(3)-C(4)-C(7) | 115.0(6) |
| C(5)-C(4)-C(7) | 119.6(5) | C(8)-C(9)-C(10) | 120.9(4) |
| C(8)-C(9)-C(18) | 117.5(4) | C(10)-C(9)-C(18) | 121.5(4) |
| C(9)-C(10)-C(11) | 126.8(4) | C(10)-C(11)-C(12) | 113.8(6) |
| C(10)-C(11)-C(19) | 107.6(6) | C(12)-C(11)-C(19) | 108.8(5) |
| C(11)-C(12)-C(13) | 115.2(5) | C(12)-C(13)-C(14) | 115.5(4) |
| C(13)-C(14)-C(15) | 114.8(4) | C(13)-C(14)-C(20) | 119.2(4) |
| C(15)-C(14)-C(20) | 125.8(5) | C(14)-C(15)-C(16) | 129.8(4) |
| C(15)-C(16)-C(17) | 115.7(4) | C(15)-C(16)-C(21) | 126.9(4) |
| C(17)-C(16)-C(21) | 117.3(4) | | |
| Cent(1)-Lu(1)-Cent(2) | 126.7 | Cent(1)-Lu(1)-Cent(3) | 128.9 |
| Cent(2)-Lu(1)-Cent(3) | 104.2 | | |

Cent(1) is the centroid of the unit defined by C(1)-C(2)-C(3)-C(4)-C(5).
Cent(2) is the centroid of the unit defined by C(8)-C(9)-C(10).
Cent(3) is the centroid of the unit defined by C(20)-C(14)-C(15)-C(16)-C(21).

TABLE V

Anisotropic displacement coefficients (Å$^2$ × 10$^4$) for $(C_7H_{11})Lu(C_{14}H_{22})$.

| | U$_{11}$ | U$_{22}$ | U$_{33}$ | U$_{23}$ | U$_{13}$ | U$_{12}$ |
|---|---|---|---|---|---|---|
| LU(1) | 205(1) | 269(1) | 337(1) | −39(1) | 22(1) | −79(1) |
| C(1) | 528(31) | 524(30) | 506(27) | −7(23) | −213(23) | −85(24) |

TABLE V-continued

Anisotropic displacement coefficients ($Å^2 \times 10^4$) for $(C_7H_{11})Lu(C_{14}H_{22})$.

| | $U_{11}$ | $U_{22}$ | $U_{33}$ | $U_{23}$ | $U_{13}$ | $U_{12}$ |
|---|---|---|---|---|---|---|
| C(2) | 392(24) | 387(23) | 496(25) | −31(19) | −15(19) | −15(19) |
| C(3) | 343(21) | 316(20) | 495(23) | −56(17) | −16(17) | −54(17) |
| C(4) | 322(22) | 423(25) | 441(23) | −44(19) | −3(18) | 27(18) |
| C(5) | 341(25) | 608(33) | 668(34) | −4(26) | 158(23) | −47(23) |
| C(6) | 788(42) | 420(27) | 617(33) | 204(24) | 167(30) | 41(27) |
| C(7) | 681(39) | 515(32) | 568(32) | −191(25) | 99(28) | 40(28) |
| C(8) | 417(24) | 395(23) | 594(27) | −59(20) | 31(20) | −222(20) |
| C(9) | 449(23) | 269(18) | 474(22) | −31(16) | −84(18) | −202(17) |
| C(10) | 484(26) | 423(23) | 425(21) | −60(18) | −109(18) | −195(20) |
| C(11) | 775(40) | 545(31) | 371(23) | −111(21) | −44(23) | −238(29) |
| C(12) | 700(39) | 718(38) | 401(24) | −181(24) | 167(24) | −256(31) |
| C(13) | 403(26) | 644(32) | 586(29) | −183(25) | 139(22) | −159(23) |
| C(14) | 230(18) | 464(24) | 531(25) | −132(20) | 40(17) | −136(17) |
| C(15) | 280(19) | 351(20) | 477(22) | −80(17) | −39(16) | −88(16) |
| C(16) | 291(20) | 385(22) | 475(22) | −92(18) | −99(16) | −91(17) |
| C(17) | 634(33) | 451(27) | 503(26) | −16(21) | −148(23) | −104(24) |
| C(18) | 641(32) | 319(21) | 544(27) | −65(19) | −68(23) | −141(21) |
| C(19) | 1536(84) | 1156(64) | 462(31) | −196(36) | −171(40) | −773(64) |
| C(20) | 355(22) | 454(24) | 548(25) | −36(19) | 40(18) | −213(19) |
| C(21) | 411(24) | 436(24) | 507(24) | −158(19) | −75(19) | −103(19) |

The anisotropic displacement exponent takes the form: $-2\pi^2(h^2 a^{*2} U_{11} + \ldots + 2hka^*b^* U_{12})$

TABLE VI

H-Atom Coordinates (33 $10^4$) and Isotropic Displacement coefficients ($A^2 \times 10^4$) for $(C_7H_{11})Lu(C_{14}H_{22})$.

| | x | y | z | U |
|---|---|---|---|---|
| H(1A) | 7 | −1272 | 3894 | 800 |
| H(1B) | 1675 | −1537 | 3187 | 800 |
| H(3A) | −918 | −3620 | 2223 | 800 |
| H(5A) | 2316 | −1146 | 1733 | 800 |
| H(5B) | 1268 | −375 | 857 | 800 |
| H(6A) | 65 | −4757 | 3979 | 800 |
| H(6B) | −1563 | −3119 | 4199 | 800 |
| H(6C) | −1938 | −4006 | 3525 | 800 |
| H(7A) | 1440 | −3754 | 664 | 800 |
| H(7B) | −797 | −3270 | 871 | 800 |
| H(7C) | −31 | −1961 | 300 | 800 |
| H(8A) | −1723 | 3425 | 1225 | 800 |
| H(8B) | −104 | 2708 | 1920 | 800 |
| H(10A) | −1540 | 2316 | 3399 | 800 |
| H(11A) | −5044 | 4187 | 3747 | 800 |
| H(12A) | −6345 | 2293 | 4574 | 800 |
| H(12B) | −4731 | 831 | 4226 | 800 |
| H(13A) | −7399 | 3321 | 3121 | 800 |
| H(13B) | −7966 | 1851 | 3619 | 800 |
| H(15A) | −6392 | 3239 | 1863 | 800 |
| H(17A) | −6532 | 3036 | 101 | 800 |
| H(17B) | −5480 | 3864 | 568 | 800 |
| H(17C) | −4257 | 2517 | 28 | 800 |
| H(18A) | −4300 | 6011 | 2274 | 800 |
| H(18B) | −4639 | 5301 | 1520 | 800 |
| H(18C) | −5720 | 5020 | 2371 | 800 |
| H(19A) | −3937 | 3059 | 5123 | 800 |
| H(19B) | −2215 | 1593 | 4802 | 800 |
| H(19C) | −2261 | 3443 | 4567 | 800 |
| H(20A) | −4829 | −987 | 3538 | 800 |
| H(20B) | −5381 | −1274 | 2677 | 800 |
| H(21A) | −4677 | −950 | 1221 | 800 |
| H(21B) | −3364 | −267 | 525 | 800 |

The invention may be embodied in other forms without departing from the spirit or essential characteristics thereof. Consequently, the present embodiments and examples are to be considered only as being illustrative and not restrictive, with the scope of the invention being defined by the appended claims. All embodiments which come within the scope and equivalency of the claims are therefore intended to be embraced therein.

I claim:

1. $(\eta^5-(CH_3)_2C_5H_5)Lu(\eta^5-,\eta-3-(CH_3)C_5H_5CH_2CH_2CH(CH_3)C_3H_3(CH_3))$.

2. A pentadienyllutetium complex according to claim 1 in crystalline form.

3. A pentadienyllutetium complex having the structural formula shown in FIG. 1.

4. A composition of matter according to claim 2 having the ORTEP diagram shown in FIG. 2.

5. A process for preparing a complex of the formula $(\eta^5-(CH_3)_2C_5H_5)Lu(\eta^5-,\eta-3-(CH_3)C_5H_5CH_2CH_2CH(CH_3)C_3H_3(CH_3))$ which comprises reacting a source of 2,4-dimethylpentadienyl anions with a source of trivalent lutetium cations.

6. A process according to claim 5 wherein said source of 2,4-dimethylpentadienyl anions is 2,4-dimethylpentadienylpotassium.

7. A process according to claim 5 wherein said source of trivalent lutetium cations is lutetium trichloride.

8. A process according to claim 5 wherein said source of 2,4-dimethylpentadienyl anions is 2,4-dimethylpentadienylpotassium and said source of trivalent lutetium cations is lutetium trichloride.

9. A process according to claim 8 wherein said 2,4-dimethylpentadienylpotassium and said lutetium trichloride are reacted in a molar ratio of about 3:1.

10. A process according to claim 5 wherein 2,4-dimethylpentadienylpotassium is reacted with lutetium trichloride in an ether solvent.

11. A process according to claim 10 wherein said solvent comprises tetrahydrofuran.

12. A process according to claim 5 wherein 2,4-dimethylpentadienylpotassium is reacted with lutetium trichloride at a temperature of about −40° C. to about −100° C.

13. A process according to claim 12 wherein said temperature is about −78° C.

14. A process according to claim 5 wherein said source of 2,4-dimethylpentadienyl anions and said source of trivalent lutetium cations are reacted in an ether solvent at a temperature of about −40° C. to about −100° C.

15. A product prepared according to the process of claim 14.

16. A process according to claim 14 which additionally comprises isolating from the reaction product a crystalline material of the formula $(\eta^5-(CH_3)_2C_5H_5-$ )Lu($\eta^5-,\eta-3-(CH_3)C_5H_5CH_2CH_2CH(CH_3)C_3H_3(CH_3)$).

17. A process according to claim 5 wherein said source of 2,4-dimethylpentadienyl anions and said source of trivalent lutetium cations are reacted in a molar ratio of about 3:1.

18. A product prepared according to the process of claim 17.

19. A product prepared according to the process of claim 8.

20. A product prepared according to the process of claim 9.

21. A process for preparing a pentadienyl lanthanide complex which comprises reacting a source of open-chain pentadienyl anions with a source of trivalent lanthanide metal cations.

22. A product prepared according to the process of claim 21.

23. A process according to claim 21 wherein said source of open-chain pentadienyl anions and said source of trivalent lanthanide metal cations are reacted in a molar ratio of about 3:1.

24. A product prepared according to the process of claim 23.

25. A process according to claim 21 wherein 2,4-dimethylpentadienylpotassium is reacted with lutetium trichloride.

26. A product prepared according to the process of claim 25.

* * * * *

UNITED STATES PATENT AND TRADEMARK OFFICE
CERTIFICATE OF CORRECTION

PATENT NO. : 5,075,426

DATED : December 24, 1991

INVENTOR(S) : Matthew B. Zielinski

It is certified that error appears in the above-identified patent and that said Letters Patent is hereby corrected as shown below:

Column 1, line 14, change "Hydrocarbyl complexes" to -- Complexes --.

Column 5, line 45, change "4246" to -- 42 --.

Column 7, in Table V, line beginning "C(10)" change "423 (23)" to -- 432 (23) --.

Column 7, Table V, line beginning "C(19)", change "-196 (36)" to -- -194 (36) --.

Column 7, in Table VI, line beginning "coefficients . . .", change "$A^2$" to -- $\overset{\circ}{A}{}^2$ --.

Signed and Sealed this

Sixth Day of April, 1993

Attest:

STEPHEN G. KUNIN

*Attesting Officer*           *Acting Commissioner of Patents and Trademarks*